(12) United States Patent
Alvarez et al.

(10) Patent No.: US 9,968,419 B2
(45) Date of Patent: May 15, 2018

(54) METHOD AND ORAL APPLIANCE FOR IMPROVING AIR INTAKE AND REDUCING BRUXISM

(71) Applicants: Ramiro Michael Alvarez, Fremont, CA (US); Jose Sergio Alvarez, Newark, CA (US); Wayne Carl La Velle, Honolulu, HI (US)

(72) Inventors: Ramiro Michael Alvarez, Fremont, CA (US); Jose Sergio Alvarez, Newark, CA (US); Wayne Carl La Velle, Honolulu, HI (US)

( * ) Notice: Subject to any disclaimer, the term of this patent is extended or adjusted under 35 U.S.C. 154(b) by 516 days.

(21) Appl. No.: 13/776,109

(22) Filed: Feb. 25, 2013

(65) Prior Publication Data

US 2013/0298916 A1    Nov. 14, 2013

Related U.S. Application Data

(63) Continuation-in-part of application No. 13/007,620, filed on Jan. 15, 2011, now abandoned.

(60) Provisional application No. 61/357,795, filed on Jun. 23, 2010.

(51) Int. Cl.
*A61C 5/14* (2006.01)
*A61F 5/56* (2006.01)

(52) U.S. Cl.
CPC ............... *A61C 5/14* (2013.01); *A61F 5/566* (2013.01); *A61F 2005/563* (2013.01)

(58) Field of Classification Search
CPC ......... A61F 5/566; A63B 71/085; A61C 5/90; A61C 7/08; A61C 7/125; A61C 9/0006
USPC .................. 128/861–862; 433/6, 19
See application file for complete search history.

(56) References Cited

U.S. PATENT DOCUMENTS

| | | | | |
|---|---|---|---|---|
| 5,194,003 A | * | 3/1993 | Garay | A61J 7/0092 433/215 |
| 5,536,168 A | * | 7/1996 | Bourke | A61F 5/01 433/24 |
| 8,075,309 B2 | * | 12/2011 | Li | A61C 19/063 433/24 |
| 2005/0241646 A1 | * | 11/2005 | Sotos | A61F 5/566 128/848 |
| 2005/0284489 A1 | * | 12/2005 | Ambis, Jr. | A63B 71/085 128/859 |

(Continued)

*Primary Examiner* — Kari Rodriquez
(74) *Attorney, Agent, or Firm* — Global Intellectual Property Agency, LLC; Daniel Enea

(57) ABSTRACT

Provided is a soft flexible oral appliance having protuberances that mimic naturally occurring dental Tori. An upper, palatial appliance and a lower, mandibular appliance may be used in conjunction or separately to alleviate a variety of disorders, improve facial tone, and increase physical performance. The appliances are lightweight, thin, and do not prohibit normal speech patterns when in use. Small protuberances are strategically molded along key surfaces of each appliance to stimulate nerves in the tongue and affect forward protrusion. Forward positioning of the tongue dilates the airways of the throat improving breathing while the use is sleeping, playing sports, or talking. It also reduces bruxing, or grinding of the teeth. A method is further provided, for adding protuberances to other types of oral appliances, thereby conferring some of the benefits listed above on appliances originally intended for other dental uses.

11 Claims, 3 Drawing Sheets

(56) References Cited

U.S. PATENT DOCUMENTS

| | | | |
|---|---|---|---|
| 2006/0289013 A1* | 12/2006 | Keropian | A61F 5/566 |
| | | | 128/848 |
| 2008/0210244 A1* | 9/2008 | Keropian | A61F 5/566 |
| | | | 128/848 |
| 2010/0147315 A1* | 6/2010 | Chodorow | A61F 5/566 |
| | | | 128/861 |
| 2012/0165862 A1* | 6/2012 | Allen | A61H 39/04 |
| | | | 606/204 |
| 2014/0190491 A1* | 7/2014 | Garcia | A61C 5/14 |
| | | | 128/861 |
| 2016/0158628 A1* | 6/2016 | Layzell | A61C 9/0006 |
| | | | 128/862 |
| 2016/0367342 A1* | 12/2016 | Alvarez | A61C 8/0083 |

\* cited by examiner

METHOD AND ORAL APPLIANCE FOR IMPROVING AIR INTAKE AND REDUCING BRUXISM

CROSS REFERENCE TO RELATED APPLICATION

This application claims the benefit of U.S. Provisional Application No. 61/357,795 filed on Jun. 23, 2010, entitled "P3 Personal Power and Performance Mouthpiece," and U.S. Non-provisional Ser. No. 13/007,620, filed on Jan. 15, 2011 entitled "P3 Personal Power and Performance Mouthpiece." For the purposes of providing a clear and continuous disclosure, the aforementioned applications are incorporated herein by reference.

BACKGROUND OF THE INVENTION

Field of the Invention

The present invention relates to a therapeutic oral appliance. More specifically, it relates to an upper and lower oral appliance having protuberances modeled after naturally occurring oral topographical elements called Tori. These protuberances cause gentle irritation of nerves innervating the dorsum and lateral surfaces of the tongue, thereby affecting forward re-positioning of the tongue. Such positioning provides a number of health benefits including improved air intake into the bronchial pathways, improved muscle tone, and reduced bruxism. A method is also provided for bonding protuberances to pre-existing oral appliances. The invention will be appreciated by athletes, people suffering from sleep disorders, speech therapy patients, and people who grind their teeth regularly.

Dental Tori are naturally occurring bumps or mounds that grow inside the mouth. These bumps are the result of bone cell deposit accumulation on specific surfaces of the oral cavity. Mandibular Tori (Tori Mandibularis) are bone growths on the lower jaw and generally occur on the anterior lingual surfaces of the mandible, near the pre-molars. In most cases, mandibular Tori are present on both sides of the mandible (left and right), though they need not be symmetrical in size or shape. Palatial Tori (Tori Palatinus) are bone growths generally occurring on the hard palate. These bumps tend to grow along the midline or anterior edges of a patient's hard palate region. They may be flat, ridged, or nodular bins shape. A third type of Tori, Buccal Tori (Buccal Exostosis) form behind the molars near the mandibular hinge. Tori are a benign and painless condition and do not generally require surgical removal unless they interfere with the use of medically necessary oral appliances such as dentures.

Though the Tori condition itself is non-threatening, the underlying causes of Tori growth may warrant medical treatment. Local stress on the jaw can initiate or increase the deposit of bone material along the surfaces of the oral cavity. Teeth grinding, known as bruxism causes repeated stress and tension to the musculoskeletal structures of the jaw. As the patient grinds his or her teeth, force is exerted in multiple directions, wearing down the teeth and causing muscle damage. If bruxism continues over a substantial period of time, the patient can suffer serious bone loss, cracked teeth, muscle dysfunction, and other health problems. Often, the symptoms are treated via the use of pain medications, muscle therapies, and nighttime oral appliances that protect the teeth and absorb shock. Treatment of the causes of bruxism can be difficult without further testing to determine whether the grinding is a result of anxiety and stress in the user's life, or if a breathing disorder such as sleep apnea is a factor.

Sleep disorders, such as obstructive sleep apnea (OSA), are strongly linked to night and daytime bruxism. Sufferers of OSA are particularly susceptible to grinding and gnashing their teeth during apnea episodes and the stress and fatigued resulting from disrupted sleep can lead to daytime grinding. OSA is a disorder in which a sleeper's breathing is interrupted by the whole or partial collapse of the pharyngeal airway of the throat. During pharyngeal constriction, breathing may be shallow or may cease all together. Abnormal breathing can last for ten seconds to several minutes. Patients may snore, make choking noises, grind their teeth or have small spasms as they try to breathe. Over time, untreated apnea can lead to the health problems associated with bruxism, heart disease, high blood pressure, stroke, memory loss, and other forms of brain damage. Treatments for obstructive sleep apnea include oral appliances that open up the mouth to allow air flow, oxygen masks that force air into the throat (continuous positive airway pressure), and lifestyle changes including dietary changes and exercise.

Oral appliances currently used in the treatment of obstructive sleep apnea or bruxism are designed to prevent the teeth from connecting, forcing the mandible forward and maintaining an opening in the mouth. This mandibular repositioning maintains the pharynx passageway in an open state, permitting continuous airflow through the passageways of the throat. While these appliances may be helpful to some patients, they physically reposition the mandible without requiring any active participation by the patient's orofacial muscles. Thus the muscles are not actually strengthened, but are merely stretched. Proper muscle tone and strengthening could reduce frequency of apnea episodes and increase the pharynx's ability to maintain dilation without mechanical support.

Flexing tongue musculature can manipulate pharynx opening size without mandible movement. The tongue has four intrinsic muscles, responsible for shaping and flexing the tongue, and four extrinsic muscles, responsible for moving the tongue within the oral cavity. Intrinsic tongue muscles are located within and along the top and margins of the tongue. Extrinsic muscles extend from a structure outside the tongue to an area within. These exterior muscles are the genioglossus, the hypoglossus, the styloglossus, and the palatioglosus. The Genioglossus extends from the mental spine of the mandible and inserts within the tongue structure along the inferior and lateral portions of the tongue. It is responsible for tongue protrusion and depression. Similarly, the hypoglossus is also responsible for depression and protrusion or retraction of the tongue. The hypoglossus extends from the great horn of the hyoid bone in the neck to the inferior and lateral surfaces of the tongue. The styloglossus muscle extends from the styloid and stylohyoid ligament into the lateral and inferior portions of the tongue. The styloglossus assists in retraction of the tongue. Lastly, the palatoglossus extends from the Palatine Aponeurosis to lateral portions of the tongue and is responsible for affecting elevation of the tongue posterior. When the genioglossus contracts, moving the tongue forward, the pharyngeal cross-section is increased. Conversely, contraction of the hypoglossus or styloglossus pulls the tongue backward into the oral cavity causing a reduction in pharyngeal cross-section.

Pharyngeal dilation can be achieved via stimulated natural tongue protrusion without mechanical repositioning of the mandible. Motor innervation for all tongue muscles comes from the hypoglossal nerve (CNXII) except for the palatoglossus, which is supplied by the pharyngeal plexus (Vagus nerve). Tongue motor function is voluntary and not regularly susceptible to reflex responses. Sensory experience of the anterior (front two-thirds) of the tongue is supplied by a branch of the trigeminal nerve (V3) known as the lingual nerve. The hypoglossal nerve and lingual nerve are in communication along the anterior border of the hypoglossal muscle. Thus, stimulation of the lingual nerve across different portions of the tongue surface can be translated to the hypoglossal nerve and affect voluntary motor function of the extrinsic muscle structures. Electrical stimulation of the genioglossus insertion into the tongue has been shown to manipulate pharyngeal cross-section size. Stimulation across the anterior portions produces genioglossus contraction and forward tongue protrusion, while stimulation of posterior areas results in bunching of the posterior tongue that constricts pharyngeal diameter. Though useful in clinical settings, electrical stimulation of a user's oral cavity during sleep or while engaging in athletics would be cumbersome if not outright dangerous. An oral appliance is needed that employs targeted physical stimulation of the tongue surface to affect dilation of the airways of the throat and improve muscle strength.

Description of the Prior Art

The present invention is a soft, flexible oral appliance having upper and lower mouthpieces that may be used in conjunction or independently. The upper mouthpiece has a teeth trough extending across the entire set of upper teeth, and a partial palatial surface extending from the lingual surface of the trough. Three sets of nodular protuberances are disposed along the palatial surface; two sets located at premolars on laterally opposing sides of the palatial surface, and one larger protuberance centrally located at an area behind the two front teeth. The lower mouthpiece has a pair of troughs extending over the mandibular molars. A facial bridge section joins the two troughs together. The lingual surfaces of each trough have a mandibular surface extending down over the mandible. Sets of nodular protuberances are disposed on these mandibular surfaces. Both the protuberances of the upper mouthpiece and those of the lower mouthpiece are positioned and shaped like naturally occurring nodular dental Tori. A method for adding protuberance sets to other types of oral appliances is also included as an aspect of the present invention. The prior art does not disclose a mouthpiece that includes specifically placed protuberances that stimulate surfaces of the tongue related to the genioglossus muscle. Nor does the prior art disclose a method for retrofitting oral appliances with artificial dental Tori.

Protective mouthpieces that cover the teeth and absorb shock are often used by people engaged in active and contact sports. Athletes such as hockey players, boxers, and football players universally use these mouth pieces during games, matches or scrimmages. When the user collides with another player, or an object, their teeth may clench, or be significantly jarred during impact. It is essential that the teeth are protected by a shock absorbent material, to reduce the risk of irreparable damage. Examples of such protective mouth pieces are described in U.S. Pat. No. 3,124,129 issued to M. E. Grossberg, on Mar. 10, 1964, and U.S. Pat. No. 3,496,936 issued to K. W. Gores on Feb. 24, 1970. These appliances or mouth pieces are bulky to protect the entire surface area of the teeth. Such mouth pieces are physically unattractive and prevent the user from speaking clearly and distinctly when in place. Consequently, the protective device must be continuously inserted or removed from the mouth during periods of non-contact when the user needs to speak. For example, most football players will hold the mouth piece in the mouth only during the actual time the play is progressing and are not held in place during the huddle or between plays. For non-impact sports, the present invention provides a lightweight, flexible oral appliance that allows the use to speak normally during use. The protuberances of the mouthpiece cause forward tongue protrusion and increase oxygen flow to the lungs and consequently the muscles. For impact sports requiring substantially thick mouth guards, the present invention provides a method for adding raised nodules to specific locations along the surfaces of the mouthpiece to provide irritants that will cause tongue protrusion and increase air flow while the user is playing a sport. The increase in air intake will result in higher blood oxygen content and thereby enhance performance and endurance.

As a further benefit to the present invention, recent studies indicated that controlled stress of selected muscles, such as the masticator muscles in the jaw, have a desirable cumulative effect on physical activity participants. That is, if particular selected muscles of the face can be brought to a selected tension or tonus, this tonus can affect other muscles of the body by increasing their tone and readiness for activity such that the athlete or wearer may achieve a competitive edge for a period of time.

Shock absorbent oral appliances are also useful for reducing the deleterious effects of bruxism. These devices act as a buffer between the teeth to disperse force during grinding. For example, U.S. Pat. No. 3,924,638 issued to G. E. Mann on Dec. 9, 1975, discloses two embodiments of such a tension relieving mouth appliance. Like the protective mouth pieces used in contact sports, these tension relieving mouth appliances are also readily visible when in place, and usually cause the user's speech to become slurred. Thus, these devices are not suitable for general daytime wear except during periods where articulation and clarity of speech are unnecessary. Such periods are few and far between in the average workplace, where most people experience stressful situations. At the very time an individual under formal stress may most need an appliance, the prior art devices are not suitable. The present invention solves this problem by providing a soft, flexible, shock absorbent device that can reduce the stress of teeth grinding. It is suitable for day or nighttime use because it does not impair speech patterns. Additionally, the device improves air intake into the lungs, oxygenating the blood and brain, which may assist in calming wearers during times of high anxiety or stress.

People with Temporal Mandibular Disorders (TMD) also experience regular teeth grinding episodes. Occlusal splints are frequently used to treat this type of bruxism. These splints function by overloading the periodontal receptors of two teeth in an arch thereby reflexly reducing the muscle force generated by the person experiencing TMD. An occlusal splint is a removable appliance that fits over the occlusal and incisal surfaces of the teeth in one arch creating precise occlusal contact with the teeth of the opposing arch. It is commonly referred to as a bite guard, night guard, interocclusal appliance, or orthopedic device. This type of splint typically can be used [1] to provide a more stable or functional joint position; [2] to introduce an optimum occlusal condition which reorganizes the neuromuscular reflex activity; or [3] to protect the teeth and supportive structures from abnormal forces which may create breakdown or tooth wear or both. [Okeson, "Fundamentals of Occlusion and Temporomandibular Disorders" (The C. V.

Mosby Company, St. Louis, 1985), page 333]. Splint therapy has also been used for treatment of Temporomandibular Disorders [TMD].

Temporomandibular Joint Disorders [TMJ] can cause headaches, jaw clenching, and bruxism. Some headaches are related to problems with the temporal mandibular joint. It has been shown that a mouth-bite splint can be fashioned to prevent a person from clenching and realizing the various symptoms of TMJ and, in particular, soft bite guards which better absorb occlusal forces by virtue of their soft nature and aid in TMD and TMJ therapy [Lucia, "Modern Gnathological Concepts—Updated" (Quintessence Publishing Co., Inc., Chicago, 1983), page 38].

The Shore Mandibular Auto repositioning Appliance [SMAA] can also aid in reducing the symptoms of TMJ and TMD. It was developed in approximately 1960. The SMAA frees the mandible from malocclusion and transmits the force of mandibular closure through the teeth to the maxilla thus removing pressures from the traumatized joints. To make the SMAA, a temporarily incorrect functional occlusion is created in acrylic. An acrylic-plate cast is made for the upper teeth, fitted to the person's teeth. An acrylic ramp [protuberance] approximately 3 mm thick is fabricated on the lingual aspect of the central incisors; Shore refers to the anti-occluder [protuberance] as a "ramp"]. The acrylic plate covers the palatal surface and the ramp acts as the splint [anti-occluder].

Snoring, upper airway resistance syndrome, and obstructive sleep apnea syndrome (OSAS) are all related to narrowing or obstruction of the upper airway during sleep (sleep disordered breathing). Very common symptoms in OSAS patients are morning headaches and acid reflux. During airway obstructions the forceful attempts to inspire air can cause tremendous negative pressure in the chest. These high negative pressures can draw acid up the esophagus from the stomach. The acid can travel all the way into the mouth and cause inflammation of the vocal cords and nasal mucosa. The presence of the acid in the upper airway causes reflex bronchoconstriction in the lung that is similar to an asthma attack.

Snoring occurs when the mouth is open and the tongue moves back into the throat. This causes the airway passage to narrow which increases the likelihood of snoring. It is known that moving the condyle of the lower jaw forward in a way will increase the airway and assist in the elimination of snoring.

Nocturnal tooth grinding (bruxing) is a major pain—the pressure is ten times the force registered during normal chewing. Bruxing causes the teeth to wear down at odd angles, affecting the shape of the face, causing migraine headaches and muscle soreness and aggravating TMJ disorders.

Most importantly, sleep disorders can cause serious medical disorders and death. Apneas cause a large strain on the heart and lungs. Over time the many repeated episodes of apnea cause chronic changes leading to hypertension. Long periods of apnea allow the oxygen levels in the blood to decrease. In turn the low oxygen can cause heart attack or stroke.

As discussed above, the protective oral appliances used to address teeth grinding and TMJ/TMD are bulky or physically manipulate the mandible into a forward position. Though this may assist with the dilation of the pharynx, and the prevention of teeth grinding, these devices must be removed before the user can speak, eat, or perform other activities. This can be a hassle when the user wakes in the middle of the night and needs to speak, drink water, or eat.

The present invention solves this problem by providing an unobtrusive oral appliance that uses gentle irritation of the tongue to affect pharyngeal dilation, without physical repositioning of the jaw. In this way, the present invention uses natural responses to assist with bruxism and apnea relief rather than forcing the oral cavity into an unnatural position for extended periods. By encouraging the tongue to move on its own, the invention provides the benefit of increased muscle strength and tone in the face and neck.

While numerous oral appliances are known in the prior art today, none have proven to be fully effective as an everyday remedy. Major reasons for the lack of wider spread use, and hence increased effectiveness, for these appliances include the negative aesthetic appeal they carry and the impact they have on speech. The present invention offers a mouthpiece that, while learning numerous aspects from the prior art, alleviates these two major downfalls. Additionally, the present invention provides a device that does not disrupt natural jaw position, and improves air intake rather than obstructing it, as some of the prior art devices do. It substantial differs in design elements from the known types of therapeutic oral appliances and thus provides a much needed improvement in the art.

SUMMARY OF THE INVENTION

In view of the foregoing disadvantages inherent in the known types of dental mouthpieces now present in the prior art, the present invention provides a new mouthpiece wherein the same can be utilized for providing convenience for the user by alleviating numerous medical conditions, improving performance, and providing unaltered speech.

The present invention is a two part oral appliance that reduces episodes of sleep apnea and bruxism by increasing pharyngeal dilation and strengthening local musculature. Clusters of protuberances are strategically disposed along lingual surfaces of the mouth guard. Specifically, the mandibular extensions and partial palatial surface are the only locations on the device where protuberances are located, because these surfaces cover parts of the mouth where dental Tori naturally grow. The protuberances are modeled after dental Tori, as small, smooth, rounded conical, or ridged lumps. Because Tori of these shapes and sizes are not harmful to the sensitive tissues of a patient's mouth, the artificial Tori can be used to gently guide the tongue without damaging the oral cavity. When the tongue is guided into a protruded, forward position, the airways of the throat expand in diameter, resulting in increased airflow. Pharyngeal dilation helps in preventing whole or partial collapse during respiration and thus reduces the regularity of sleep apnea episodes.

A method is also provided for adding protuberances to mouthpieces that were originally created for other uses. An orthodontic resin is mixed and then applied in mounds to areas corresponding to the rim of the hard palate and lingual mandibular surfaces. The device is then cooked to set the resin. Resin is sanded and molded into small nodular protuberances at key locations along the chosen surfaces. Though these modified oral appliances may still prevent normal speech patterns or have unaesthetic appearances, they will acquire some of the increased air intake benefits of the present oral appliance.

It is therefore an object of the present invention to provide a dental mouthpiece that can alleviate numerous the symptoms associated with night time sleep disorders.

Another object of the present invention is to provide a mouthpiece that can improve performance in athletes during daytime use by facilitating increased oxygen intake.

Yet another object of the present invention is to provide a mouthpiece that can protect the teeth, mandible, and muscles against teeth clenching in high stress situations (i.e. CPAP combination therapy).

Still another object of the present invention is to provide a two part oral appliance having parts that can be used independently or in conjunction to reduce occurrences of sleep apnea and improve oxygen intake.

A further object of the present invention is to provide an oral appliance that mimics naturally occurring oral topographic elements to gently irritate the tongue and affect forward protrusion.

A still further object of the present invention is to provide a method for retro-fitting preexisting oral appliances with nodular protuberances that mimic naturally occurring dental Tori formations.

Other objects, features and advantages of the present invention will become apparent from the following detailed description taken in conjunction with the accompanying drawings.

BRIEF DESCRIPTIONS OF THE DRAWINGS

Although the characteristic features of this invention will be particularly pointed out in the claims, the invention itself and manner in which it may be made and used may be better understood after a review of the following description, taken in connection with the accompanying drawings wherein like numeral annotations are provided throughout.

DETAILED DESCRIPTION OF THE INVENTION

Figure 1:
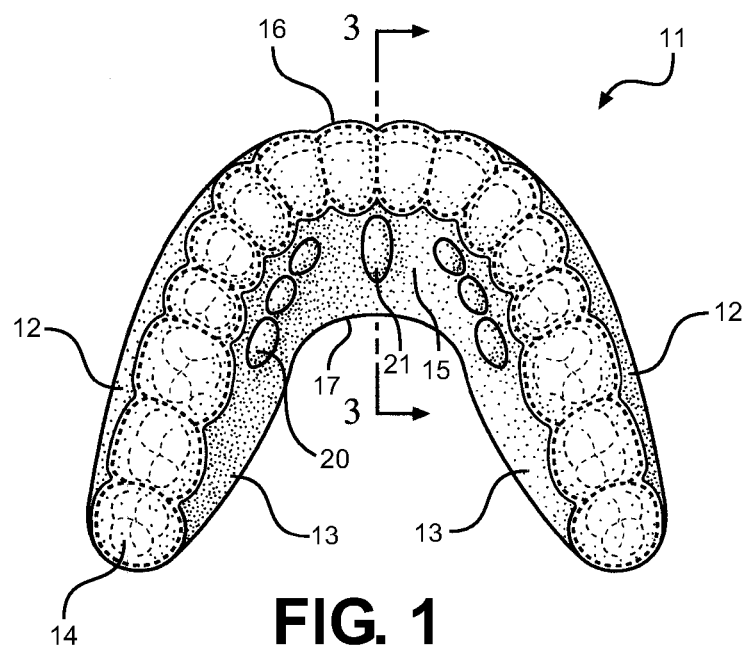
FIG. 1 shows a top view of the upper mouthpiece of the oral appliance. Three groupings of protuberances are visible on the left, anterior, and right portions of the partial palatial surface.

Reference is made herein to the attached drawings. Like reference numerals are used throughout the drawings to depict like or similar elements of the therapeutic oral appliance. For the purposes of presenting a brief and clear description of the present invention, the preferred embodiment will be discussed as used for improving air intake, reducing instances of sleep apnea and bruxism. The figures are intended for representative purposes only and should not be considered to be limiting in any respect.

Referring now to FIG. 1, there is shown a top view of the upper mouthpiece 11 of the oral appliance. The upper mouthpiece 11 is a single piece appliance made of soft resilient material. It comprises a dental trough that covers the teeth of the upper mouth, extending from posterior molars on one side of the mouth to posterior molars on the other side. The area of the mouthpiece located in the forwarded most region of the mouth is denoted as the anterior surface. The anterior surface comprises lingual 15 and facial surfaces 16. The left and right sides and back of the mouthpiece are denoted as the posterior surface. The posterior surface comprises facial 12, lingual 13, and occlusal 14 surfaces. Facial surfaces terminate along a user's gum line, where the teeth meet the soft gum tissue. Conversely, the lingual surfaces extend past the gum line up onto the hard palate, creating a partial palatial region that ends at a terminating edge 17 of the lingual surface. This partial palatial region is an extension of the lingual surfaces and does not cover a user's entire hard palate like some medical retainers. Precise proportions of the partial palatial region will vary according to the specific anatomy of the patient. In the figure, the lingual surface is shown extending beyond the dental trough, with a greater thickness in the anterior region than in the posterior regions. It is desired that the posterior of the mouth should remain free of irritants to the extent possible as stimulation of posterior areas of the tongue can affect retraction or convexing of the tongue rather than the desire effect of depressed protrusion.

Two lateral clusters of protuberances 20 and one central protuberance 21 are disposed along the partial palatial region of the anterior lingual surface 15 of the mouthpiece to gently irritate the anterior portions of the dorsum (upper layer of the tongue). This irritation stimulates the lingual nerve near intrinsic musculature responsible for widening and flattening the tongue and near the genioglossus insertion into the lateral portions of the anterior tongue. Stimulation of lingual nerve branches is communicated to the brain and hypoglossal nerve, which then affects voluntary motor function of the nearby musculature. The wearer may experience a feeling that the tongue is "worrying" or "messing" with the protuberances. This activity causes the tongue to protrude and obtains the desired effect of increased pharyngeal cross-section.

A central protuberance 21 is located on the partial palatial region of the anterior lingual surface. As a general guide, the central protuberance is aligned between the two incisors. The central protuberance 21 is oblong, with a dorsal ridge. This shape is selected because Tori Palantinus forming along the midline of the hard palate tend to have either a large flat shape with a wide diameter, or more commonly, a sloped, ridge shape. The smooth, oblong shape of the central protuberance is thus an artificial rendering of the natural shape of midline palatial Tori. Further, the dorsal ridge Is useful in guiding the tongue forward along the midline, as opposed to a raised rounded protrusion in this area which the tongue may ignore or move around.

Three smaller, rounder protuberances forming a lateral protuberance cluster 20 are located on the partial palatial region of the left and right anterior lingual surface 15. These protuberances are conical or domed in shape, mimicking the nodular Tori that sometimes grow on the palate away from the midline. Each of the lateral clusters forms a barrier that prevents the tongue from maneuvering around the central protuberance 21. If the wear tries to move his or her tongue to either side of the central protuberance instead of moving forward, the lateral portions of the anterior dorsum will encounter a lateral protuberance cluster. This will irritate local branches of the lingual nerve, which will by communication with the hypoglossal nerve, cause the lateral intrinsic musculature to curl the margin of the tongue and force it back towards the center. In this way, the lateral protuberance clusters are guides that prevent the tongue from straying off course as it becomes irritated by the central protuberance. It is not desirable for a single elongated wall-like protuberance to replace the small, nodular protuberances, because such a large structure would likely over stimulate the lateral regions of the dorsum and affect retraction. Nodular Tori are a naturally occurring phenomenon within the mouth and in most cases do not obstruct regular tongue function. It is desirable that the protuberances of the present invention are modeled as closely as possible after small, naturally occurring shapes and dimensions of dental Tori. The specific positioning of the protuberances will depend on the topography of a patient's hard palate and tongue size, but as a general guide the first protuberance is located at a cuspid tooth, the second protuberance is located at a first bicuspid tooth, and the third protuberances located at a second bicuspid tooth. Patients with small tongues or large hard palate surface area, may warrant repositioning of the protuberances to ensure that all three groupings, central and both lateral clusters, are molded so as to be positioned within the anterior one-third of the user's mouth when the mouthpiece is in place.

Each of the protuberances 20, 21 will have a height of 1 mm to 5 mm, which depends upon the tongue response and topography of the patient's mouth. Cases where the arch of the hard palate is higher than average, may necessitate protuberances having a height greater than 5 mm, and one of ordinary skill in the creation of oral appliances will be able to readily determine if such a palate abnormality exists. As mentioned above, protuberances may be tuned to a specific individual and may therefore vary in size and shape relative to each other or be of substantially the same size and shape. Tuning may include increasing or decreasing the diameter of a single protuberance as well as increasing or decreasing the general roundness of a single protuberance. It should be understood that all protuberances are smooth without distinct edges that can damage the sensitive tissues of the oral cavity. Jagged or rough areas can cause abrasion over time and will cause the tongue to avoid the protuberance containing the rough spots. This is counterproductive as it directs the tongue away from an area that might otherwise be used to guide the tongue forward.

Figure 2:
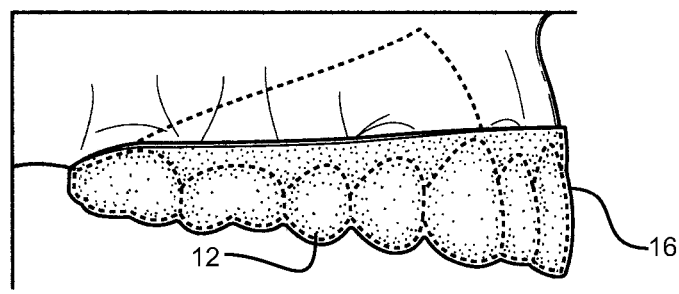
FIG. 2 shows a side view of the upper mouthpiece fitted around upper teeth. The facial surface of the oral trough is visible, snuggly fitted to the surface of the teeth.
Figure 3:
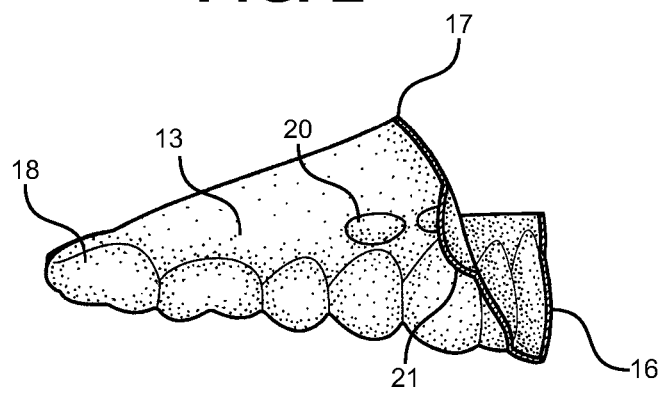
FIG. 3 shows a cross section cut of the upper mouthpiece. The central protuberance and two of the lateral cluster protuberances are visible along the partial palatial surfaces.

FIGS. 2 and 3 illustrate how the lingual surface 13 of the mouthpiece extends down to the gum line of the molar 18. From the molar 18 to the incisors, the lingual surface gradually slopes past the gum line to cover the hard palate of the mouth. FIG. 2 illustrates the facial surfaces 12, 16 stopping at the gum line.

FIG. 3 shows a cross sectional view through the central protuberance 21. The protuberance 21 can be seen protruding into the user's mouth and extending from the gum line to the hard palate. This positioning is suggested, however it may be necessary to move the central protuberance away from the gum line and further onto the partial palatial region of the anterior lingual surface 15. While placement of the protuberances should not be narrowly limited to the exact positioning shown here, it should be noted that the protuberances will never be located on the portion of the lingual surfaces associated with the teeth trough. Further, the protuberances will never be located on the facial surfaces. The facial surfaces 12, 16 of the mouthpiece stop at the gum line, whereas the partial palatial region extends onto the hard palate and has a surface area that is largest at the anterior lingual surface and tapers in palate coverage as the terminating edge 17 moves toward the most posterior lingual surfaces, those covering the molars 18. This configuration reduces the risk of undesirable irritation of posterior portion of the tongue near insertion of styloglossus and palatoglossus, which would cause the tongue to retract.

Figure 4:
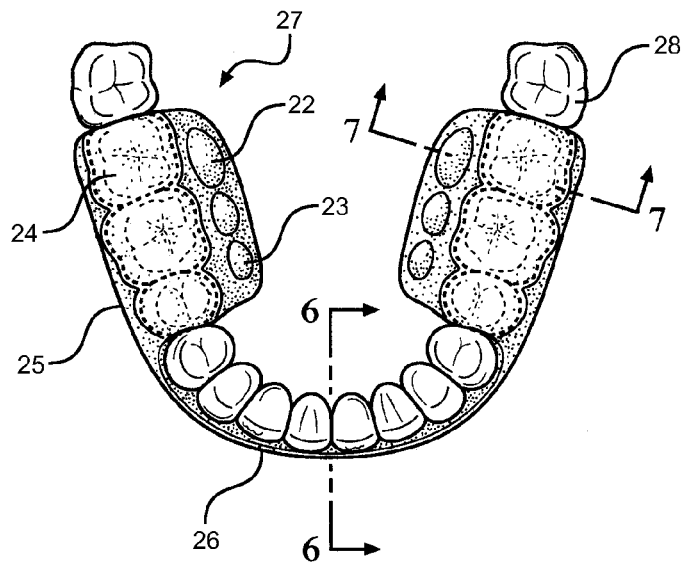
FIG. 4 shows a top view of the lower mouthpiece fitted around lower teeth. Two lateral clusters of protuberances are disposed on the mandibular extensions of the two dental troughs.

FIG. 4 shows a top view of the lower mouthpiece 27. The lower mouthpiece 27 is a single piece appliance made of soft resilient material. It has two dental troughs connected by an anterior facial bridge portion 26. These dental troughs are bite sections that cover the second molar, first molar, and second premolar on the left and right sides of the mouth. They extend to, but do not cover, the third molar 28. Each bite section has a facial surface 25, a lingual surface 23 and an occlusal surface 24, wherein the three surfaces form a trough covering these three teeth. The facial surface 25, 26 extends the entire mouthpiece, reaching down to the gum line at each tooth. An anterior facial bridge is created via the anterior facial surface 26 and extends between the lower facial surfaces of the two dental troughs. The bridge covers only the gum line of the teeth in order to be discrete and reduce or prevent impairment of the wearer's speech. Anterior bridges should not be placed lingually because this creates an irritant along the lingual gum line. The tip of the wearer's tongue will investigate this gum line irritant and will be forced to flex convexly. Such flexing obstructs the airways of the throat and is therefore undesirable.

Figure 5:
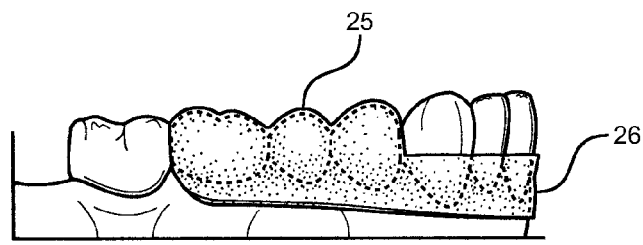
FIG. 5 shows a facial side view of the lower mouthpiece fitted over teeth. A bridge section extends across the facial gum line and joins the two dental troughs.
Figure 6:
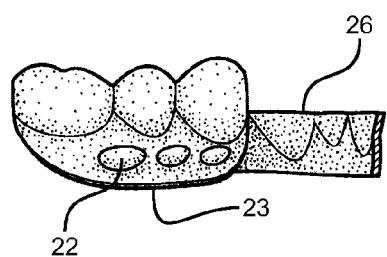
FIG. 6 shows a lingual side view of the lower mouthpiece. One cluster of protuberances sticks up from the surface of the mandibular extension.

FIG. 5 shows the anterior surface 26 covering only the gum line area of a user's mouth. FIG. 4 and FIG. 6 show the lingual 23 and occlusal 24 surfaces, which are only present at the bite section of the mouthpiece. The lingual surfaces extend down onto the gum tissue covering the lingual mandible. Portions of the lingual surfaces that do not touch the teeth, but extend over the mandible are mandibular extensions. Like the partial palatial region of the upper mouthpiece, the mandibular extensions are regions of the lingual surface that are positioned over gum tissue, in areas of the mouth where dental Tori most commonly grow.

A plurality of protuberances grouped in lower lateral clusters 22 are formed on the left and right mandibular extensions of the lingual surface. On each side a protuberance is located on the mandibular extension below the first molar, second molar, and second premolar. Natural occurrences of Tori Mandibularis are generally positioned near the pre-molars. The lower lateral protuberances of the present invention are positioned at these locations so as to create artificial dental Tori that will not abrade the tongue or disrupt its normal function. These nodular protuberances gently irritate lingual nerve branches in the lateral portions of the inferior tongue, which communicates the irritation to the brain and hypoglossal nerve. Motor function of the genioglossus muscle is then initiated, moving the tongue forward. Genioglossus insertion occurs along the inferior and lateral tongue, making stimulation of this area particularly effective for achieving forward repositioning. Some patients may find that independent use of the lower mouthpiece provides better results than independent use of the upper mouthpiece; however this will vary according to anatomy of different users.

It will be understood by one of ordinary skill in the art that the lower lateral protuberance clusters may be shifted slightly toward the anterior of the mouth. While anterior shifting may be necessary to achieve proper genioglossus motor function for some patients, posterior shifting should be avoided. As is shown in FIGS. 4 and 6, the third protuberance extends to, but not past the first molar. Placement of protuberances near the rear molars or further back will result in stimulation of the lingual nerve branches innervating the hypoglossus and cause the wear to retract his or her.

Figure 7:
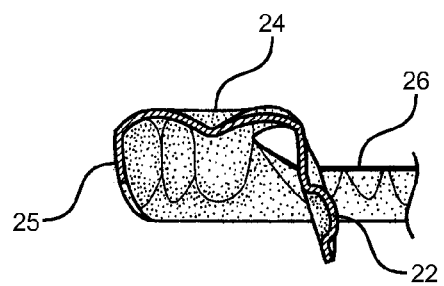
FIG. 7 shows a cross sectional back view of the bite section on the lower mouthpiece. The mandibular protuberances extend away from the dental trough as smooth lumps.

FIG. 7 depicts a cross sectional view of the left side, looking forward, wherein a protuberance 22 at the second molar is shown. The mandibular extension of the lingual surface 23 extends from the gum line down onto the mandible and should have a gum line to lower edge width equal to or greater than the protuberance 22 diameter. These three protuberances 22 can be of substantially the same diameter and shape, or may vary with respect to each other as well as with respect to the protuberances 20, 21 on the upper mouthpiece. In general, the height of each protuberance will be between 1 mm and 5 mm. They may be domed, conical, or oblong as all these shapes occur in mandibular Tori. Like the upper mouthpiece protuberances, the lower protuberances should be smooth and even surfaces with no rough or jagged edges.

Patients may utilize either one, or both of the mouthpieces to alleviate sleep apnea, reduce bruxism, and improve muscle tone. As discussed above, the Tori-like protuberances of the present invention gently irritate the anterior dorsum and/or lateral inferior tongue, making the wearer want to move the tongue forward within the oral cavity. This is an exercise in targeted micromuscle manipulation. While the patient is wearing the mouthpiece he is consciously or subconsciously flexing and contracting various muscles within the tongue, throat, and face. Movement and manipulation will tone and strengthen the associated musculature. Strengthening these muscles will improve overall breathing capabilities and may lead to reduced need for nighttime use of the mouthpiece, because the throat muscles may grow strong enough to remain dilated without intervention. These results will vary based on user anatomy and the underlying causes of the apnea. Secondly, those wearing the oral appliance to reduce damage associated with bruxism, will appreciate the soft, and shock absorbent construction that cushions their teeth from pressure. The forward protrusion of the tongue caused by the protuberances will open up the bite slightly, making it difficult for the wearer to clamp his teeth down and grind. In this way, the mouthpieces can alleviate both the symptoms of bruxism and help reduce the user's ability to grind the teeth. Bruxism associated with sleep apnea is treated by reducing occurrences of nighttime apnea episodes. For those wearers who use the device to improve physical performance, the effects of strengthened facial and throat muscles will be obvious as they experience increased air intake and eased swallowing. Thus, the present oral appliance provides a wide variety of benefits to wearers.

Figure 8:
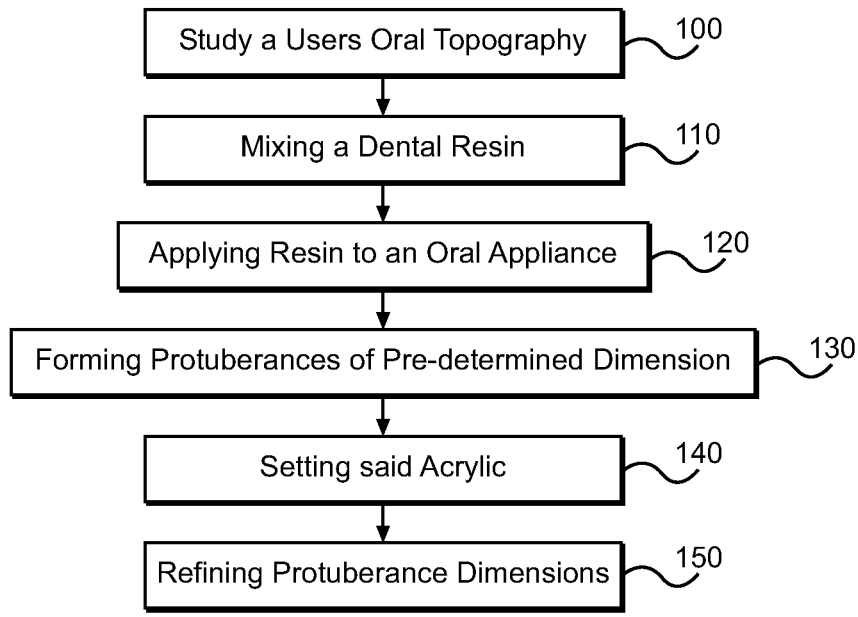
FIG. 8 shows a flow chart diagram of the mound formation process of the present invention.
Figure 9:
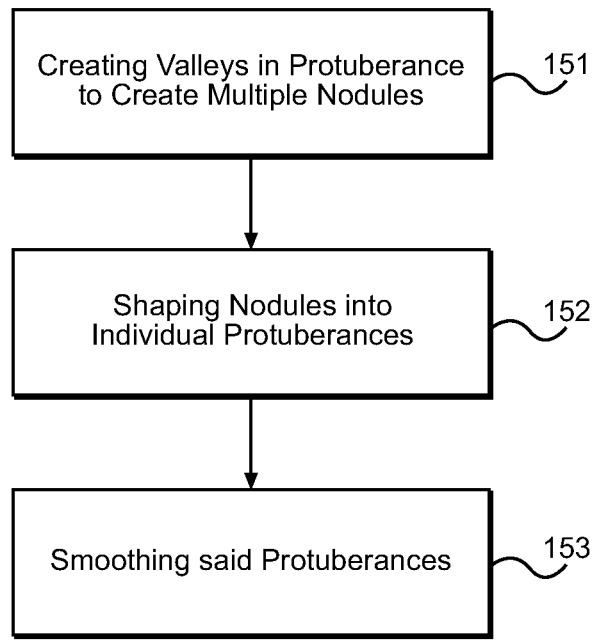
FIG. 9 shows a flow chart diagram of the protuberance shaping and refinement process of the present invention.

The appliance described herein is the preferred configuration, but the addition of strategically placed protuberances to other oral appliances may convey some of the benefits. Modification of other appliances is achieved through application of dental resin to the appliance to form mounded protuberances. This process is illustrated in FIGS. 8 and 9.

First, the dentist, or other dental professional measures the topography of the patient's mouth 100. This can be done by creating a mold of the mouth and teeth, imaging the area, or by taking physical measurements. By determining where the anterior and posterior tongue rest within the oral cavity, and its positioning with respect to the patient's teeth, the dentist can figure out the proper placement of the protuberances. The oral appliance is marked, to indicate this positioning and may be applied to a model to ensure correctness of markings.

Next, an orthodontic resin such as dental acrylic is mixed 110. Most dental resins are transported in powder form for easy storage. Liquid monomer acrylic is added to the powder and stirred, to create a tacky, deformable resin. Using a metal spatula or other suitable applicator, the dental professional applies the dental resin to marked areas of the appliance 120. It may be applied in domes or mounded regions. Before the resin has time to set, a moistened cotton swab is used to shape the applied resin into protuberances 130. This will include the, smoothing of the sides, and may call for the addition or removal or resin. The resulting protuberances should have the generally desired shape and size but do not need to be perfectly dimensioned because refinement will occur at the end of the process.

The oral appliance, with newly applied dental resin is then placed in a pressure pot until the dental resin partially sets 140. After setting, the resin will still be malleable, and ready for finalization of the protuberances. The protuberances of the oral appliance are refined 150 through gentle application of pressure to the thick resin. Once again a moistened cotton swab is useful for this step. First the dental professional creates valleys in the unfinished protuberance 151, thereby forming multiple nodules from one protuberance. These nodules are then manipulated and shaped into individual protuberances 152. Shapes of the variety disclosed above are contemplated, such as oblong, domed, conical, and ridged. Once the desired height and shape is obtained, the protuberances are smoothed to eliminate rough spots or jagged edges. The oral appliance is set in the pressure pot until fully and then cooled.

Wearers of the modified oral appliance will experience forward tongue protrusion and thus increased air intake. The extent of dilation will be affected by the configuration of the oral appliance. In this way, a patient having a medically necessary oral appliance will be able to experience increased air flow without having to switch the necessary oral appliance out for the mouthpieces of the present invention.

In use an individual places the upper mouthpiece in the oral cavity with the protuberances extending downward. He aligns the dental trough with his teeth then gently pushes upward on different sections of his teeth until the mouthpiece snuggly abuts the teeth surfaces. Next, the lower mouthpiece is placed in the oral cavity with the protuberances extending upward. The two dental troughs are aligned with the user's pre-molars and first molar and then gently pressed downward. An anterior facial bridge will fit snuggly against the facial gum line of the lower teeth, connecting the two dental troughs. The upper and lower teeth may be gently pressed together to mash the mouthpieces in place. Once the two pieces of the oral appliance are in place the user can participate in activities as normal. Sports, meetings, sleeping, or any other activity can be enjoyed without impaired speech or fear of bruxism damage. It conveys a number of health benefits, and reduces instances of sleep apnea.

The present invention is a two part oral appliance and method of retrofitting protuberances to an oral appliance. The upper and lower mouthpieces may be worn individually or in conjunction. In many patients, benefits will be experienced with the use of either mouthpiece individually. The lower mouthpiece in particular is well suited for individual use because it does not cover the anterior teeth and therefore is not visually unappealing. Both mouthpieces are constructed of a soft, flexible, shock absorbent material. They are clear or highly translucent and have a thickness of a few millimeters, making them visually unobtrusive when worn.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

We claim:

1. A soft resilient performance increasing and therapeutic mouthpiece for removably attaching to upper teeth of a user, comprising:
    facial and lingual anterior surfaces, facial and lingual posterior surfaces, and an occlusal surface, wherein said surfaces are connected to form a trough, said trough being molded to conform to a wearer's teeth;
    said facial surfaces and said lingual surfaces being contoured to match the wearer's teeth;
    said lingual surfaces having a partial palatial region that is configured to extend from a lingual gum line over a portion of a hard palate, wherein a distance between said lingual gum line and a terminating edge of said partial palatial region of said lingual surfaces is greatest at said anterior lingual surface and tapers towards said posterior lingual surfaces;
    a central protuberance extending from said partial palatial region of said lingual surfaces, said central protuberance having an oblong shape with a dorsal ridge, wherein said central protuberance is positioned over an anterior midline of the wearer's hard palate when in use;
    two lateral protuberance clusters extending from laterally opposing sides of said partial palatial region of said lingual surfaces, each comprising three nodular protuberances, wherein said clusters are positioned on said partial palatial region so as to interact with anterior margins of a dorsum of a wearer's tongue when in use.

2. The device of claim 1, wherein said lateral protuberance clusters are comprised of domed protuberances.

3. The device of claim 1, wherein said central protuberance and said lateral protuberance clusters are between 1 mm and 5 mm in height.

4. The device of claim 1, wherein every surface has a thickness of 5 mm or less.

5. A soft resilient performance increasing and therapeutic mouthpiece for removably attaching to the lower teeth of a user, consisting of:
    two dental troughs, each having a lingual surface, a facial surface, and an occlusal surface that form a trough covering a second molar, a first molar and a second premolar of a user's mouth;
    an anterior facial surface connecting said facial surfaces of said dental troughs, wherein said anterior facial surface is shorter in height than said facial surfaces of said dental troughs, and wherein said anterior facial surface covers only a facial gum line when in use;
    said lingual surfaces each having a mandibular extension region, adapted to extend from a lingual gum line down over a lingual portion of the mandible, and wherein said mandibular extension regions extend further below a gum line than said facial surfaces when in use;
    a pair of lower lateral protuberance clusters, each of said lower lateral protuberance clusters extending from one of said mandibular extension regions of said lingual surfaces, and comprising three nodular protuberances.

6. The device of claim 5, wherein said protuberances are between 1 mm and 5 mm in height.

7. The device of claim 5, wherein every surface has a thickness of 5 mm or less.

8. The device of claim 5, wherein said lateral protuberance clusters are comprised of domed protuberances.

9. A soft resilient performance increasing and therapeutic oral appliance comprising:
    an upper mouthpiece having facial and lingual anterior surfaces, facial and lingual posterior surfaces, and an occlusal surface, wherein said surfaces are connected to form a trough, said trough being molded to conform to a wearer's teeth;
    said upper mouthpiece facial surfaces and said upper mouthpiece lingual surfaces are contoured to match the wearer's teeth;
    said upper mouth piece lingual surfaces having a partial palatial region that is configured to extend from a lingual gum line over a portion of a hard palate, wherein a distance between said lingual gum line and a terminating edge of said partial palatial region of said upper mouthpiece lingual surfaces is greatest at said anterior lingual surface and tapers towards said posterior lingual surfaces;
    a central protuberance extending from said partial palatial region of said upper mouthpiece lingual surfaces, said central protuberance having an oblong shape with a dorsal ridge, wherein said central protuberance is positioned over an anterior midline of the wearer's hard palate when in use;
    two lateral protuberance clusters extending from laterally opposing sides of said partial palatial region of said upper mouthpiece lingual surfaces, each comprising three nodular protuberances, wherein said clusters are positioned on said partial palatial region so as to interact with anterior margins of a dorsum of a wearer's tongue when in use; and
    a lower mouthpiece having two dental troughs, each having a lingual surface, a facial surface, and an occlusal surface that form a trough covering a second molar, a first molar and a second premolar of a user's mouth;
    a lower mouthpiece anterior facial surface connecting said facial surfaces of said dental troughs, wherein said lower mouthpiece anterior facial surface is shorter in height than said facial surfaces of said dental troughs, and wherein said lower mouthpiece anterior facial surface covers only a facial gum line when in use;
    said dental trough lingual surfaces each having a mandibular extension region, adapted to extend from a lingual gum line down over a lingual portion of the mandible, and wherein said mandibular extension regions extend further below a gum line than said facial surfaces when in use;
    a pair of lower lateral protuberance clusters, each of said lower lateral protuberance clusters extending from one of said mandibular extension regions of said dental trough lingual surfaces, and comprising three nodular protuberances.

10. The device of claim 9, wherein said protuberances are between 1 mm and 5 mm in height.

11. The device of claim 9, wherein every surface has a thickness of 5 mm or less.

\* \* \* \* \*